United States Patent [19]

Olney

[11] Patent Number: 5,474,990

[45] Date of Patent: Dec. 12, 1995

[54] BARBITURATES AS SAFENING AGENTS IN CONJUNCTION WITH NMDA ANTAGONISTS

[76] Inventor: John W. Olney, 1 Lorenzo La., Ladue, Mo. 63124

[21] Appl. No.: 734,210

[22] Filed: Jul. 22, 1991

Related U.S. Application Data

[63] Continuation-in-part of Ser. No. 424,548, Oct. 20, 1989, Pat. No. 5,034,400.

[51] Int. Cl.⁶ .......................... A61K 31/54; A61K 31/44; A61K 31/445; A61K 31/515

[52] U.S. Cl. .................. 514/226.2; 514/270; 514/289; 514/315; 514/318

[58] Field of Search .................. 514/226.2, 270, 514/289, 315, 318

[56] References Cited

U.S. PATENT DOCUMENTS

| | | |
|---|---|---|
| 3,930,006 | 12/1975 | Wiggins et al. .................. 514/270 |
| 4,064,139 | 12/1977 | Anderson et al. .................. 514/906 |
| 4,374,838 | 2/1983 | Anderson et al. .................. 514/289 |
| 4,399,141 | 8/1983 | Anderson et al. .................. 514/294 |
| 4,833,148 | 5/1989 | Olney .................. 514/270 |
| 4,888,347 | 12/1989 | Woodruff et al. .................. 514/289 |

*Primary Examiner*—Raymond Henley, III
*Assistant Examiner*—K. Weddington
*Attorney, Agent, or Firm*—Patrick D. Kelly

[57] ABSTRACT

Certain barbiturates have been shown to completely prevent the neurotoxic injury to cerebrocortical neurons that can be caused by NMDA antagonists. The use of barbiturates as "safening agents" allows NMDA antagonists (including powerful NMDA antagonists such as MK-801) to be used safely as neuroprotectants to prevent brain damage due to hypoxia/ischemia caused by strokes, cardiac arrest, perinatal asphyxia, and various other conditions.

16 Claims, 1 Drawing Sheet

BARBITURATES AS SAFENING AGENTS IN CONJUNCTION WITH NMDA ANTAGONISTS

This application is a continuation-in-part of U.S. application Ser. No. 07/424,548, filed on Oct. 20, 1989, which issued as U.S. Pat. No. 5,034,400.

BACKGROUND OF THE INVENTION

This invention is in the fields of pharmacology and neurology. It relates to two different classes of receptors on the surfaces of neurons, known as NMDA receptors, which are triggered by N-methyl-D-aspartate (NMDA), and GABA receptors, which are triggered by gamma-aminobutyric acid (GABA).

This invention involves the use of NMDA antagonists (i.e., agents which block activity at NMDA receptors) as therapeutic agents which can prevent excitotoxic brain damage and nerve cell death during stroke, cardiac arrest, perinatal asphyxia, drowning, and various other events. Unfortunately, the currently available NMDA antagonists, when used for such purposes, exert toxic side effects that can kill or permanently damage neurons in certain regions of the brain.

This invention relates to the discovery that certain types of barbiturates which function as GABAmimetic agents (i.e., they trigger activity at GABA receptors) function as "safening agents" to reduce the damaging side effects of NMDA antagonists. By reducing the damage caused by NMDA antagonists, the barbiturates disclosed herein allow the safe use of NMDA antagonists to treat stroke, cardiac arrest, and other conditions.

To understand the processes and interactions involved, some background information is necessary on NMDA and GABA receptors, and on various types of molecules that stimulate or suppress activity at those receptors.

Receptors, messenger molecules, agonists, and antagonist

The surfaces of nerve cells in the central nervous system (the CNS, which includes the brain, spinal cord, and retina) contain various types of receptor molecules. In general, a receptor molecule is a polypeptide that straddles a cell membrane. When a messenger molecule interacts with the exposed extracellular portion of the membrane receptor molecule, it triggers a difference in the electrochemical status of the intracellular portion of the receptor, which in turn provokes some response by the cell. The messenger molecule does not bond to the receptor; instead, it usually disengages from the receptor after a brief period and returns to the extracellular fluid. Most receptor molecules are named according to the messenger molecules which bind to them.

An "agonist" is any molecule, including the naturally occurring messenger molecule, which can temporarily bind to and activate a certain type of receptor. An agonist can cause the same effect as the natural messenger molecule, or in some cases it can cause a more intense effect (for example, if it has a tighter affinity for the receptor molecule and remains bound to the receptor for a prolonged period). By contrast, an "antagonist" is a molecule which can block or reduce the effects exerted by the natural messenger molecule.

The role a specific molecule plays as an agonist or antagonist must be viewed with regard to a certain type of receptor. For example, while PCP and MK-801 are antagonists for the NMDA receptor, they are agonists for the PCP receptor (both types of receptors are discussed below). Most agonists and antagonists are xenobiotic drugs, i.e., they do not exist naturally in the body.

Membrane receptors involved in the transmission of nerve impulses between neurons are divided into two main categories: excitatory receptors, and inhibitory receptors. In general, excitatory receptors initiate or facilitate the conduction of nerve impulses. The principle class of excitatory receptors is referred to as "excitatory amino acid" (EAA) receptors, or as "glutamate" receptors. EAA receptors are important to this invention, and they are discussed below. A second major class of excitatory receptors, called cholinergic receptors, are activated by acetylcholine. They are discussed in the co-pending parent application, which issued as U.S. Pat. No. 5,034,400. That patent describes the use of anti-cholinergic drugs as safening agents to reduce the neurotoxic side effects of NMDA antagonists. Since the invention discussed below does not heavily involve cholinergic receptors or anti-cholinergic drugs, they are not discussed in detail herein.

In contrast to excitatory receptors, inhibitory receptors help to suppress the initiation or conduction of nerve impulses. Inhibitory receptors include GABA receptors, which are highly important in this invention, as well as other types of receptors that are not important herein, such as dopamine, serotonin, and opiate receptors. GABA receptors are discussed below, under their own heading.

For more information on neuroanatomy, neurotransmitters, receptors molecules, and agonists and antagonists which interact with CNS receptors, see Adelman 1987 (complete citations are provided below).

Excitatory amino acids (EAA's) and neurotoxicity

Two molecules that are highly important in the functioning of the CNS are glutamate and aspartate, which together are called excitatory amino acids (EAA's). Both molecules are found naturally in high concentrations in the central nervous system (CNS), where they function as excitatory neurotransmitters. Since glutamate is the predominant excitatory neurotransmitter, the following discussion will focus primarily on it.

Under normal conditions, when glutamate is released into a synaptic junction between two neurons, it reacts with and triggers an EAA receptor. This event is the key step in the process of neurotransmission. The glutamate is then transported back inside a neuron by means of a transport mechanism that requires energy. Glutamate is not allowed to accumulate in the synaptic fluid, since it would generate spurious and undesirable messages. However, under severe low energy conditions such as hypoxia/ischemia (as occurs in various conditions such as stroke), the transport system that normally transports glutamate back into neurons lacks sufficient energy to function properly.

For its energy needs, the brain is totally dependent on oxygen and glucose. Since the brain contains virtually no reserve supply of carbohydrates, it must rely on oxygen and glucose supplied by the blood. Hypoxia refers to a state of inadequate oxygen, and ischemia refers to inadequate blood supply (which directly entails a reduced supply of oxygen and glucose). Hypoxia and ischemia are encountered in various conditions such as stroke, cardiac arrest, loss of blood due to an injury, anemia, carbon monoxide poisoning, drowning, suffocation, or perinatal asphyxia.

When energy deficiency associated with hypoxia or ischemia impairs the glutamate transport system, glutamate accumulates in synaptic junctions and excessively stimulates EAA receptors. When a receptor-bearing neuron is excessively excited by this process, it discharges its own glutamate onto EAA receptors on other neurons. This leads to an "excitotoxic" process involving a cascade of increasing glutamate release, as more and more neurons become overstimulated and begin firing in an uncontrolled manner until they literally excite each other to death. This process can result in widespread cell death that extends well beyond the initially affected area, and if not interrupted, can result in the death of the animal or person.

As used herein, the word "excitotoxic" refers to the process by which excitatory amino acids (primarily glutamate and aspartate) kill neurons by means involving excessive excitation. Since neurons in the CNS are not regenerated after they die, excitotoxic cell death leads to permanent and irreversible brain damage even if the person or animal survives. As an example, babies that suffer perinatal asphyxia often go through their entire lives with severe and crippling cerebral palsy, even though the disruption of oxygen supply to their brains may have lasted for only a few minutes.

In addition to their role in brain damage associated with hypoxia and ischemia, glutamate and aspartate are also believed to be implicated in various other neurological disorders involving the death of neurons, including alcoholism, epilepsy, trauma of the brain or spinal cord, and slowly developing neurodegenerative disorders such as Huntington's, Parkinson's and Alzheimer's diseases.

Other mechanisms by which EAA's can cause neuronal injury include abnormal sensitivity of EAA receptors to the excitatory action of EAA's, and the presence of abnormal molecules (such as glutamate analogs, certain types of food poisons, etc.) with excitotoxic properties. In some cases, such receptor-triggering molecules can accumulate at EAA receptors because they are not recognized by the cellular transport systems as molecules which should be removed from the extracellular fluid.

Glutamate and asparate are sometimes called "endogenous" excitotoxins, meaning that they are naturally synthesized and maintained in significant concentrations within the CNS. By contrast, if glutamate or aspartate or their excitotoxic analogs are ingested in foods or administered systemically, they are referred to as "exogenous" excitotoxins.

For two review articles which summarize numerous reports on excitotoxicity, see Olney 1989 and Rothman and Olney 1986.

EAA receptors, also known as glutamate receptors, are categorized into three subtypes. Each receptor type is named after a glutamate analog that selectively excites that particular class of receptor: N-methyl-D-aspartate (NMDA), kainic acid (KA), and quisqualate (QUIS). Glutamate is capable of activating all three receptor subtypes. Since NMDA receptors are the predominant type, KA and QUIS receptors are often grouped together and called non-NMDA receptors. QUIS receptors are sometimes called AMPA receptors, because AMPA was recently shown to trigger these receptors with greater specificity than quisqualate.

In the various neurotoxic situations, a major method of preventing or minimizing excitotoxic injury to the neurons involves administering drugs that selectively block or antagonize the action of the excitotoxic molecules at the EAA receptors.

NMDA Antagonists: MK-801, PCP, etc.

The EAA receptor subtype that has been implicated most frequently in neurodegenerative diseases and neurotoxicity is the NMDA receptor. An entire issue of *Trends in Neurosciences* (Vol. 10, Issue 7, July 1987) was devoted to review articles pertaining to the NMDA receptor, and to NMDA "antagonists" (i.e., molecules which can block or reduce the effects of NMDA agonists, including glutamate, at NMDA receptors).

Agents which act by binding directly to NMDA receptors, such as D-2-amino-5-phosphonopropanoate (D-AP5) and D-2-amino-7-phosphonoheptanoate (D-AP7), are referred to as "competitive" NMDA antagonists. Those two compounds are of limited therapeutic utility because they do not readily penetrate the blood-brain barrier. However, some competitive NMDA antagonists, including 2-amino-4-methyl-5-phosphono-3-pentenoic acid (common name CGP 37849), 4-phosphonomethyl)-2-piperidinecarboxylic acid (common name CGS 19755; Boast 1988) and 3-(2)-carboxypiperazine-4-yl)-propyl-1-phosphonate (common name CPP) and its unsaturated analog, CPP-ene (Herrling et al 1989 and Aebischer et al 1989) appear to permeate mammalian BBB's in sufficient quantity to affect the CNS after administration of relatively large quantities.

The NMDA receptor complex is also believed to contain at least two other binding sites, the glycine binding site and the polyamine binding site (reviewed in Olney 1989). Several drugs reportedly block activity at NMDA receptors by binding to those sites, and accordingly are regarded as non-competitive NMDA antagonists. Two drugs which reportedly bind to the polyamine site include 4-benzyl-alpha-(p-hydroxy-phenyl)-beta-methyl-1-piperidine-ethanol (commonly called ifenprodil) and (±)-2-(4-chlorophenyl)-4-[(4-fluorophenyl)methyl]-1-piperidine ethanol (commonly called SL-82.0715; Carter et al 1988 and 1989). Certain halogenated analogs of kynurenic acid, such as 7-chloro-kynurenate, are believed to bind to the glycine binding site, as well as to KA and QUIS (non-NMDA) receptors.

The most powerful and effective NMDA antagonists known at the present time act at another receptor, the phencyclidine (PCP) receptor, which is considered a component of an ion channel complex coupled to the NMDA receptor (Kemp et al 1987). These compounds are called "non-competitive" NMDA antagonists because they do not compete for binding sites at NMDA receptors. When phencyclidine or its analogs activate the PCP receptor, the flow of ions through the NMDA ion channel is blocked, so that when the NMDA receptor is activated by an EAA, the NMDA receptor response does not result in the flow of ion currents. This prevents the excitation of the neuron.

Four compounds which can activate the PCP receptor, and which therefore serve as non-competitive NMDA antagonists, are phencyclidine, MK-801, ketamine, tiletamine, and dextromethorphan. Each is discussed in more detail below. All of these agents can penetrate the blood-brain barrier.

Phencyclidine (PCP) was originally introduced into clinical medicine some 30 years ago as an anesthetic (Goodman and Gilman 1975). Shortly thereafter, it was withdrawn from the market because it was found to have hallucinogenic properties that invited illegal use by drug abusers.

MK-801 is a phencyclidine analog manufactured by Merck, Sharp and Dohme (Rahway, N.J.). The chemical name is 5-methyl-10,11-dihydro-5H-dibenzo[a,d]cyclohepten-5,10-imine. MK-801 is discussed in U.S. Pat. Nos. 4,064,139 (Anderson et al 1977), 4,374,838 (Anderson et al 1983), 4,399,141 (Anderson et al 1983), and 4,888,347 (Woodruff et al 1989). The maleate salt of MK-801 is commonly called dizocilpine, and is available for animal research. Although MK-801 was briefly tested as an anticonvulsant in human clinical trials, it was soon withdrawn from further testing on humans, with no published explanation. More recently, MK-801 underwent preliminary testing in human trials in England as a neuroprotective agent against stroke. Again, it was withdrawn from testing with no published explanation. Subsequently, after the publication of a report (Olney et al 1989; also see Allen and Iversen 1990 and the accompanying response by Olney) which documented neuronal damage in the cingulate and retrosplenial cortices caused by MK-801, phencyclidine, ketamine, and tiletamine, the U.S. Food and Drug Administration effectively declared a moratorium on any testing of NMDA antagonists in humans. Despite its side effects, MK-801 continues to generate great interest among neurology researchers, since it is the most powerful NMDA antagonist known and since it is highly selective for the PCP receptor.

Ketamine, a drug manufactured by Parke Davis and marketed under the trade name Ketalar, is another non-competitive NMDA antagonist which activates PCP receptors (Kemp et al 1987). It is widely used in human and veterinary medicine as an anesthetic, largely because it is rapidly cleared from the system and has relatively brief, non-lingering effects and because it does not compromise cardiorespiratory functions. However, in humans, as the anesthesia wears off and the patient awakens, symptoms such as unpleasant dreams or visions, excitement, and occasionally irrational behavior occur in some patients (*Physicians Desk Reference*, 1990, p. 1616). Such symptoms are often referred to as a "ketamine emergence reaction." Currently, the widely accepted treatment to suppress these symptoms involves the administration of minor tranquilizers such as diazepam, a benzodiazepine drug that is widely sold under the trademark "Valium". In 1989 it was reported that ketamine, when administered at relatively high doses, can cause permanent neuronal damage in the cingulate and retrosplenial cortex regions of the brain, in a manner comparable to PCP and MK-801 (Olney et al 1989).

Tiletamine is a drug manufactured by A. H. Robins. It is currently used in veterinary medicine, and is widely used for anesthesia on house pets. Like PCP, MK-801 and ketamine, tiletamine is known to activate PCP receptors and is recognized as a non-competitive antagonist of the NMDA receptor-ion channel complex. Tiletamine was also tested and shown to cause neuronal damage in the cingulate and retrosplenial cortices, as reported in Olney et al 1989.

Dextromethorphan is also known to bind to PCP receptors, but it binds more weakly than any of the other four agents listed above, and it was not tested in the experiments discussed in Olney et al 1989. It also binds to a receptor known as the sigma opiate receptor, which is similar in some respects to the PCP receptor. Dextromethorphan is an ingredient in various cough syrups, some of which are illicitly abused by teenage drug users.

Because of its great potency and the ease with which it penetrates blood brain barriers, MK-801 has become the drug used most widely in animal experiments aimed at testing the neuroprotective properties of NMDA antagonists. Since it has been shown to protect CNS neurons against numerous types of degenerative processes including hypoxia/ischemia, prolonged seizures, hypoglycemia, thiamine deficiency, and head or spinal cord trauma, there is great interest in using MK-801 or other NMDA antagonists to prevent or minimize brain damage in humans.

However, the potential therapeutic uses of NMDA antagonists must be viewed with caution, because such agents can inflict their own type of neurological damage, as discussed below. The subject invention involves a class of "safening" agents that can be administered along with NMDA antagonists, to reduce or eliminate the dangers and deleterious side effects of NMDA antagonists without interfering with their beneficial effects.

The term "safening agent" is used herein to refer to a chemical that can reduce one or more adverse effects of another chemical. This term is borrowed from other fields of chemistry such as agricultural chemistry, where safening agents are applied to crop seeds or plants to give crops a high level of resistance to a herbicide. This allows the herbicide to be used at a concentration that is highly effective against weeds, while minimizing the adverse effects of the herbicide on the crop plants.

In an analogous manner, anticholinergic drugs (described in U.S. Pat. No. 5,034,400) and certain types of barbiturates (described herein) can be used as safening agents in conjunction with NMDA antagonists. These safening agents protect the CNS against adverse side effects (discussed below) caused by NMDA antagonists. This allows NMDA antagonists to be used safely and effectively as beneficial neuroprotective agents.

Neurotoxic side effects of NMDA antagonists

One of the potentially serious side effects of MK-801, phencyclidine, ketamine, and tiletamine is that they have been shown to damage certain types of neurons. In a series of experiments, MK-801, phencyclidine, and ketamine were given to adult rats to test for neuroprotection against seizure-related brain damage (Clifford et al 1989). Those NMDA antagonists did protect neurons in certain brain regions; however, they also caused adverse reactions in two highly important regions of the brain, the posterior cingulate cortex and the retrosplenial cerebral cortex (Olney et al 1989).

One neurotoxic reaction, which was observed during microscopic analysis of CNS tissue after the rats were sacrificed, consisted of the formation of vacuoles (membrane-enclosed spaces in the cytoplasm that are not present in normal cells) and the dissolution of mitochondria (energy-producing organelles inside the cells). Although these changes appeared to be reversible if the doses of MK-801 or phencyclidine were sufficiently low, it was subsequently discovered that irreversible necrosis of cingulate cortical neurons followed the administration of 5 mg/kg MK-801. In adult rats, the $ED_{50}$ for producing vacuoles in cingulate neurons by MK-801 administration (i.e., the dosage of MK-801 which will produce vacuoles in 50% of the animals treated) is 0.18 mg/kg, injected intraperitoneally (Olney et al 1989). Since the doses of MK-801 used in animal experiments for protecting neurons against ischemic brain damage usually are in the range of 1 to 10 mg/kg, it appears that the use of MK-801 for therapeutic neuroprotection poses a major risk of inducing potentially serious neurotoxic side effects.

A second indication of neuronal injury induced by NMDA antagonists involves the appearance of proteins called "heat shock protein" (HSP) in the cingulate and retrosplenial cortical neurons that are vulnerable to the toxic vacuole reaction. Heat shock proteins are often expressed in cells that are subject to severe stress (Currie and White 1981). They were first noticed in cells that were immersed in water that was nearly but not quite hot enough to kill the cells, which explains the name "heat shock". Two major types of heat shock proteins have been detected in mammals, one having a molecular weight of about 72 kilodaltons, the other having a molecular weight of about 90 kd. The 72 kd type (which presumably varies somewhat between different mammalian species) has been detected in the brains of people who died of Alzheimer's disease. Sharp et al 1990 reported that a 72 kd HSP was expressed in the brains of rats treated with MK-801. Based on that abstract, the Inventor used an antibody binding technique to confirm that 72 kd HSP's were expressed in cingulate and restrosplenial cortical neurons in treated animals; the HSP response remained detectable over a two week period.

The Inventor has shown that the pathomorphological side effects (vacuoles and mitochondrial dissolution) and the HSP response caused by NMDA antagonists can both be prevented by anticholinergic agents. This suggests that the two pathological reactions may have a common mechanism, and the finding that anticholinergic agents can protect against the pathomorphological and HSP side effects of NMDA antagonists is of considerable importance in a therapeutic context, since it permits NMDA antagonists to be used with improved safety as neuroprotective drugs. It also indicates that the mechanism of NMDA antagonist neurotoxicity involves both the blockade of the NMDA class of EAA receptors, as well as activation of the M-1 subtype of muscarinic cholinergic receptor (the order of potencies of anticholinergic drugs for preventing NMDA antagonist neurotoxicity parallels the order of binding affinities of those drugs to M-1 receptors).

As mentioned previously, MK-801 and phencyclidine are non-competitive NMDA antagonists; they bind to the PCP receptor, which is part of the NMDA ion channel complex, but they do not bind directly to the NMDA receptor itself. The Inventor has also studied the question of whether competitive NMDA antagonists (agents that bind directly to the NMDA receptor protein) can also cause pathomorphological effects comparable to the adverse effects of non-competitive NMDA antagonists, and the evidence indicates that competitive NMDA antagonists cause the same type of neurotoxic side effects. For example, microinjection of a competitive NMDA antagonist (D-AP5), which normally does not penetrate the BBB, into the cingulate cortical region (Labruyere et al 1989) caused the same type of vacuole reaction induced by MK-801 or PCP. Similarly, intravenous injection of CPP, a competitive NMDA antagonist that does penetrate blood-brain barriers to a significant extent, also causes the same vacuole reaction that is induced by PCP or MK-801. These results suggest that any antagonist which blocks NMDA receptor ion channel functioning by any mechanism is likely to cause adverse side effects. An important implication of this finding is that recently developed competitive NMDA antagonists which may be able to penetrate the blood-brain barrier (BBB) in sufficient concentration to be used as neuroprotective drugs, such as CGS 19755, CPP, and CPP-ene, might not provide a safe alternative to the non-competitive NMDA antagonists, unless anti-cholinergic drugs or the barbiturates disclosed herein are used as safening agents.

Non-NMDA Receptors and Broad-Spectrum EAA Antagonists

As mentioned previously, KA and QUIS (AMPA) receptors are often grouped together and called non-NMDA receptors. They have a higher degree of cross-reactivity with each other than either type has with NMDA receptors; most compounds that activate KA receptors also have some degree of affinity for QUIS receptors, and vice-versa. As used herein, "non-NMDA antagonist" refers to any compound that can suppress activity at either KA or QUIS receptors, or both.

Several compounds have been shown to have broad-spectrum activity in blocking all types of EAA receptors (i.e., both NMDA and non-NMDA receptors). Such compounds include kynurenic acid and its halogenated analogs (such as 7-chlorokynurenate), and certain types of thiobarbiturates (especially thiamylal).

Another class of compounds called quinoxalinediones has been discovered to have a high degree of antagonistic activity at non-NMDA receptors (Honore et al 1988). Some of these compounds also display blocking activity at NMDA receptors. Although some types of quinoxalinedione (including 6-cyano-7-nitro-quinoxaline-2,3-dione (common name CNQX) and 6,7-dinitro-quinoxaline-2,3-dione (common name DNQX) do not appear to be able to penetrate blood-brain barriers in quantities sufficient to make them effective inside the CNS, a third type of quinoxalinedione reported in 1989, 6-nitro-7-sulfamoyl-benzo(f)quinoxaline-2,3-dione (common name NBQX, also designated as FG 9202) penetrated BBB's in sufficient quantities to have a significant effect inside the CNS (Honore et al 1989 and Sheardown et al 1989).

The Inventor has demonstrated that blockage of both NMDA and non-NMDA receptors by a mixture of MK-801 and a quinoxalinedione provided better and more effective protection against hypoxic/ischemic (excitotoxic) damage to the CNS than either agent could provide by itself. That discovery is described in co-pending U.S. patent application Ser. No. 467,139, the contents of which are hereby incorporated by reference.

The GABA Receptor Complex

The $GABA_A$ receptor complex (also called the GABA-benzodiazepine receptor) is a complicated multi-component entity, reviewed in Zorumski and Isenberg 1991. It is believed to contain three or more interrelated binding sites.

One of the receptor binding sites is triggered by GABA (gamma-amino-butyric acid), an inhibitory neurotransmitter that is synthesized inside certain neurons. After release into a synaptic junction, GABA reacts with the GABA receptor protein, activating the receptor and triggering the opening of a chloride ion channel. The opening of the chloride channel allows chloride ions to enter the neuron. This results in a polarization of the neuronal membrane in the synaptic region, which temporarily inhibits the ability of the neuron to conduct bioelectric impulses. After activating its receptor, the GABA molecule is rapidly transported back into the cell and/or degraded by an enzyme called GABA transaminase.

A second binding site in the GABA receptor complex is called the benzodiazepine receptor. As indicated by the name, it is activated by benzodiazepine drugs, such as diazepam (Valium). When the benzodiazepine binding site is activated, it increases the flow of chloride ions through the GABA complex ion channel. By potentiating (increasing) the nerve signal suppression effects of GABA, benzodiazepine drugs such as Valium function as sedatives, "anxiolytic" (anxiety-suppressing) and anti-convulsant agents. Benzodiazepines can potentiate (strengthen) the chloride channel opening properties of GABA, but they cannot open the chloride channels by themselves in the absence of GABA. Therefore, they are said to possess "indirect" GABA agonist activity. By contrast, barbiturates act as "direct" GABA agonists, as discussed below.

A third protein receptor site in the GABA receptor complex, called the t-butylbicyclophosphorothionate binding site, is believed to interact with barbiturate drugs such as pentobarbital, secobarbital and thiamylal. Although the mechanism involved at that binding site is poorly understood, activation of that receptor is associated with the sedative and possibly the anti-convulsive effects of barbiturates. As mentioned previously, at least some barbiturates are capable of acting as "direct" agonists at the GABA receptor; they can cause the chloride channel of a GABA receptor to open, even in the absence of GABA. This has been demonstrated by "voltage clamp" experiments using cultured neurons, discussed in various articles such as MacDonald and Barker 1978 and Akaike et al 1987.

A fourth binding site, called the gamma-butyrolactone binding site, has also been suggested. When activated by alpha-substituted gamma-butyrolactones, it apparently increases the effects of GABA.

$GABA_A$ receptor complexes are also believed to be involved in reactions involving other psychoactive agents, including alcohol and steroid anesthetics. It should also be noted that if any of the $GABA_A$ receptor sites are blocked by agents such as bicuculline or picrotoxin, adverse responses such as anxiogenesis or convulsions can result.

An entirely different class of GABA receptor complexes are activated by an anti-spasticity drug, baclofen. Those receptor complexes are designated as $GABA_B$ receptors. They appear to be insensitive to benzodiazepines and barbiturates. Since $GABA_A$ complexes are believed to be the major sites of action for the drugs involved in this invention, $GABA_B$ complexes will not be discussed in any detail herein. Any references herein to GABA sites, or to GABAergic or GABAmimetic agents, refer to $GABA_A$ receptor complexes and to agents that interact with such receptors.

Drugs that act at the GABA receptor complex (at any of the binding sites) and mimic or increase the inhibitory effects of GABA are often called "GABAmimetic" agents. A related term, "GABAergic," is usually used to refer to components of the GABA transmitter system, such as GABAergic neurons, axons, or synapses.

It is not entirely clear how activity at the benzodiazepine, butylbicyclophosphorothionate, or butyrolactone binding sites potentiate the effects of GABA, and various mechanisms may be involved. Some drugs are believed to prolong the amount of time that a molecule of GABA remains attached to the GABA receptor. Other agents may function by means such as enlarging the diameter of the ion channel, or by increasing the amount of time that the chloride channel remains open.

GABA receptor complexes are important to the subject invention because the Inventor has found that certain GABAmimetic barbiturates can decrease both the pathomorphological and the HSP effects of NMDA antagonists in vulnerable neurons. Of particular note is the fact that GABAmimetic barbiturates completely block the neurotoxic side effects of MK-801, a powerful NMDA antagonist, whereas benzodiazepines such as diazepam (Valium) provide only partial protection.

Barbiturates

Following common usage, "barbiturate" is used herein to include analogs of barbituric acid which have sedative-hypnotic (anesthetic) or anticonvulsant effects in mammals. Barbiturates have the following general structure:

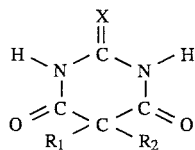

where X is oxygen (in the case of most barbiturates, such as secobarbital or pentobarbital) or sulfur (in the case of thiobarbiturates such as thiamylal), and where $R_1$ through $R_4$ are hydrogen atoms or organic groups.

Barbiturates have long been used for anesthetic purposes. However, at anesthetizing dosages, they frequently interfere with respiration, so they must be used in conjunction with mechanical respiratory devices, often called ventilators.

Most barbiturates are referred to as "anesthetic barbiturates." This distinguishes them from a separate class of non-anesthetic barbiturates such as phenobarbital, an anticonvulsant that does not have the same type of anesthetic effects that most barbiturates have. For more information on the distinctions between anesthetic and anticonvulsant barbiturates, see MacDonald and Barker 1978.

As mentioned above, some types of barbiturates have been shown to be in vitro tests to be "direct" agonists at the GABA receptor, in the sense that they can cause the opening of the chloride channel of a GABA receptor complex even in the absence of GABA. Although not all barbiturates have been tested for this property, to the best of the Inventor's knowledge, all of the barbiturates which have demonstrable potency as direct GABA agonists have been anesthetic barbiturates, while anticonvulsant barbiturates such as phenobarbital lack potency as either direct GABA agonists or as anesthetics. Accordingly, there appears to be a correlation between anesthetic activity and direct GABA agonist activity. In the absence of evidence to the contrary, a barbiturate that falls within the anesthetic category can be presumed to be a direct GABA agonist.

It has been shown that some anesthetic barbiturates also function as EAA antagonists; i.e., they can block the excitatory action of glutamate at EAA receptors. U.S. Pat. No. 4,833,148 (Olney 1989) discloses the use of thiobarbiturates as EAA antagonists to reduce neurotoxic damage due to hypoxia and ischemia, as evidenced by the ability of barbiturates to protect chick retina tissue in vitro against neurotoxicity caused by addition of NMDA, kainic acid, quisqualic acid, or glutamate to the tissue culture liquid or by ischemia which is simulated by the removal of oxygen and glucose from the culture medium. The apparent basis for the efficacy of barbiturates in conferring such protection is that they block all EAA receptors (both NMDA and non-NMDA); under ischemic conditions, as simulated in the retina tissue tests, the excitotoxic process is triggered by glutamate acting at all EAA receptor types. Thiamylal was shown to be more effective than the other barbiturates tested in protecting against glutamate toxicity or simulated ischemic damage. This is consistent with the finding that thiamylal was more potent than other barbiturates in blocking both NMDA and non-NMDA receptors.

Neither barbiturates nor diazepam have been used with NMDA antagonists for the purpose of preventing pathomorphological neurotoxic side effects of NMDA antagonists. However, there is a long tradition of using diazepam (Valium) or other benzodiazepines together with ketamine in human anesthesia. Benzodiazepines (particularly diazepam) are considered the agents of choice by anesthesiologists for suppressing the psychotomimetic side effects of ketamine. This practice is based on a series of studies over the past 15 years in which benzodiazepines have been shown to be moderately effective in reducing the incidence of emergence reactions that occur in some patients anesthetized with ketamine. In most studies, benzodiazepines have been reported to moderately reduce the severity or incidence of emergence reactions rather than totally prevent such reactions.

In the voluminous literature pertaining to use of benzodiazepines for suppressing ketamine-induced emergence reactions, including recent review articles, no mention is made of any studies in which barbiturates were tested for this purpose. However, a computerized literature search revealed that in 1974, two doctors in Nigeria reported that a thiobarbiturate, thiopentone (called thiopental in the United States) was effective in reducing ketamine-induced emergence reactions in a group of 50 women who were undergoing minor gynecological surgery (Magbagbeola and Thomas 1974). Although Magbagbeola and Thomas stated that no respiratory problems were encountered at the relatively low doses of thiopental they used (between 2 and 3 mg/kg), respiratory interference by barbiturates is a major concern whenever barbiturates are used; by contrast, diazepam provides a method of suppressing ketamine emergence reactions without raising any questions or concerns regarding respiration. Neither the Nigerian doctors nor anyone else ever followed up the 1974 report with additional reports containing more evidence for the efficacy of barbiturates in suppressing emergence reactions when using ketamine for anesthetic purposes, and there is no indication in the literature that anesthesiologists currently use barbiturates for this purpose.

It should also be noted that the Nigerian report involved the use of 2 to 3 mg ketamine per kilogram of patient body weight, to anesthetize or sedate female patients for "minor gynecological operations." The 2 mg/kg dosage provoked the transient unpleasant sensations known as ketamine emergence reaction in a fraction (less than half) of the patients studied. By contrast, the minimum dosage which reliably caused vacuole formation in cingulate neurons in rats was more than 40 mg/kg, which is in the range of ketamine dosages used in rats to achieve anti-ischemic protection.

It should also be pointed out that, because of their activity as NMDA antagonists, barbiturates should be expected to produce the same adverse side effects as other NMDA antagonists, and to aggravate those side effects when co-administered with other NMDA antagonists. However, the Inventor has discovered that barbiturates do not produce such side effects; instead, they function as safening agents which reduce or eliminate the adverse side effects of NMDA antagonists, apparently because in the cingulate and retrosplenial cortex where the adverse side effects are seen, their strong agonist activity at GABA receptors overrides their antagonist activity at NMDA receptors.

The discovery that barbiturates which act as direct GABA agonists can reduce or prevent the neurotoxic side effects of NMDA antagonists is the essence of this invention. NMDA antagonists can be highly useful therapeutic agents in various neurological disorders, but suitable agents and methods are needed to reduce or prevent the adverse side effects of NMDA antagonists.

Therefore, one object of this invention is to provide effective safening agents that can be used in both human and veterinary medicine to reduce the neurotoxicity of NMDA antagonists such as MK-801 or PCP, thereby allowing NMDA antagonists to be used more safely as anesthetics, or as neuroprotective agents to prevent neuronal death due to stroke, cardiac arrest, perinatal asphyxia, and other conditions.

Another object of this invention is to disclose that certain barbiturates effectively and reliably prevent the pathomorphological and heat shock protein reactions caused by NMDA antagonists, which affect neurons in the cingulate and retrosplenial cortex.

Another object of this invention is to provide a mixture of an NMDA antagonist combined with a barbiturate safening agent. Such mixtures can be used to prevent or reduce damage to the CNS resulting from stroke, cardiac arrest, neonatal asphyxia, and numerous other neurological diseases, trauma, and degenerative processes.

SUMMARY OF THE INVENTION

Certain barbiturates have been shown to completely prevent the neurotoxic injury to cerebrocortical neurons that can be caused by NMDA antagonists. The use of barbiturates as "safening agents" allows NMDA antagonists (including powerful NMDA antagonists such as MK-801) to be used safely as neuroprotectants to prevent brain damage due to hypoxia/ischemia caused by strokes, cardiac arrest, perinatal asphyxia, and various other conditions.

DESCRIPTION OF THE PREFERRED EMBODIMENTS

Figure 1:
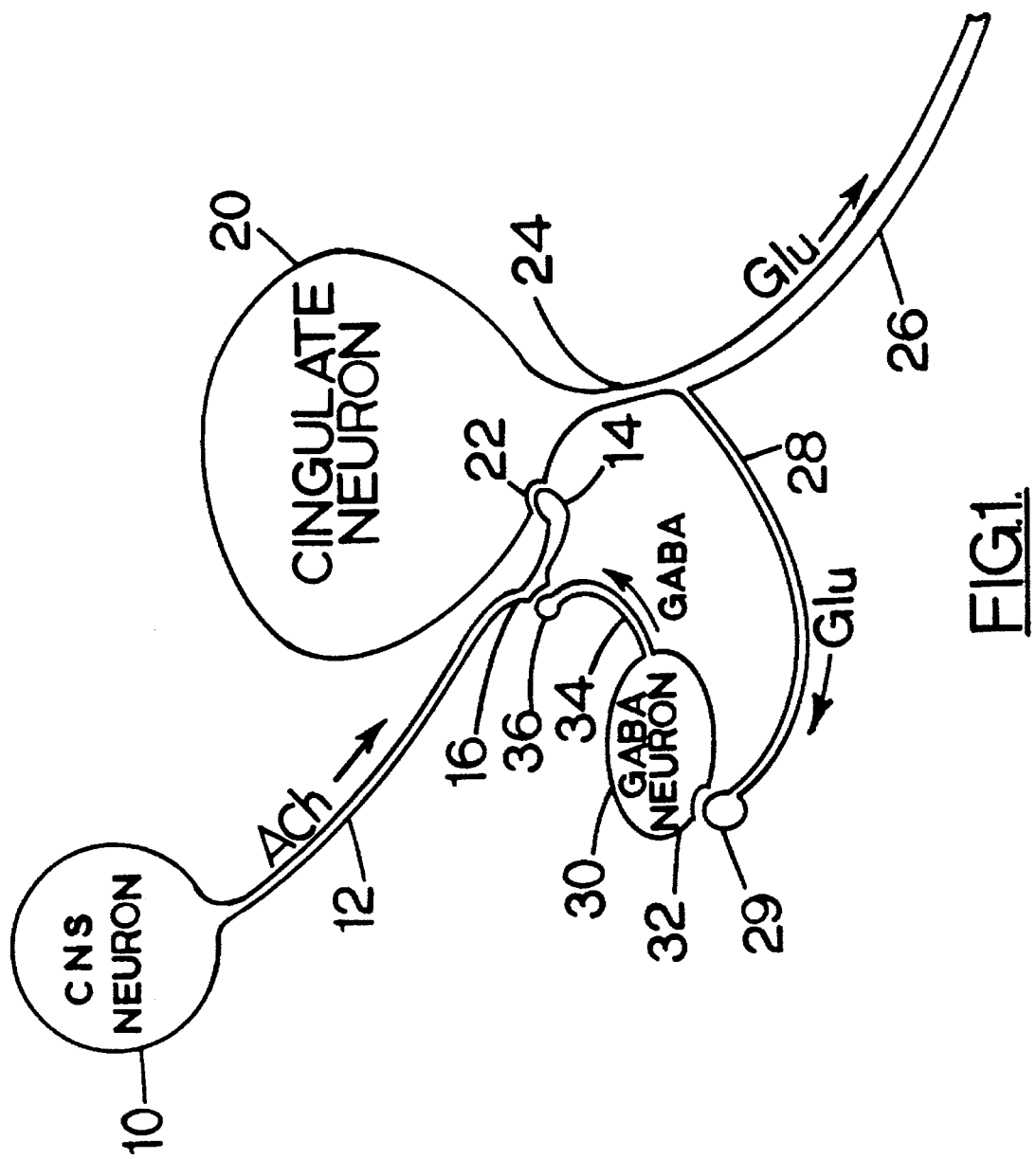
FIG. 1 is a simplified depiction of a set of neuronal connections involving acetylcholine, glutamate, and GABA receptors.

This invention relates to the use of barbiturates in conjunction with NMDA antagonists. The barbiturates act as safening agents to reduce or prevent the neurotoxic side effects of NMDA antagonists, thereby allowing the safe use of NMDA antagonists in human or veterinary medicine.

Barbiturates that act as direct agonists at GABA receptors are preferred for use as safening agents to accompany NMDA antagonists. As discussed above, anesthetic barbiturates are presumed to act as direct agonists at GABA receptors, while non-anesthetic barbiturates such as phenobarbital are not presumed to act as direct GABA agonists. Accordingly, anesthetic barbiturates are preferred for evaluation for use as described herein. However, the correlation between anesthetic activity and GABA agonist activity has not been extensively tested, and it is not critical to this invention; any specific type of barbiturate can be tested by routine experimentation using laboratory animals, as described below, to determine whether it is effective and reliable as a safening agent for use with a specific type of NMDA antagonist.

As used herein, the term "neurotoxic side effects" caused by NMDA antagonists refers to one or more of the following: (1) the formation of observable vacuoles in neurons in one or more regions of the brain; (2) damage to, dissolution of, or other significant alterations in mitochondria in CNS neurons; (3) the induction of heat shock proteins in CNS neurons; or (4) the death of, or necrotic signs in, CNS neurons. These manifestations (and the ability of specific barbiturates to prevent these manifestations) can be assessed using laboratory animals that have been treated with NMDA antagonists. The detection of vacuoles is a simple matter, requiring only light microscopy using properly prepared tissue sections, and it has been found to be a reliable indicator of neuronal damage. Other manifestations can require more effort to detect; mitochondrial damage usually requires examination with an electron microscope, and the presence of heat shock proteins requires antibody binding and detection techniques.

In order to assist readers who are not familiar with the neurons and receptors involved in this invention, the drawing in FIG. 1 is offered as a highly simplified depiction of three interacting neurons. The validity of the invention described herein does not depend upon this drawing, which is merely a caricature; nevertheless, this depiction may be helpful to some readers.

In FIG. 1, a CNS neuron 10, which is presumably located somewhere in the brain other than in the cingulate/retrosplenial (C/RS) cortex, interacts with a cingulate neuron 20 by means of an axon 12. Axon 12 is a fibrous projection that is part of CNS neuron 10. For simplicity, axon 12 is shown as terminating in a single synaptic terminal 14; in reality, a single axon often branches out into dozens of branches, and each branch usually interacts with a different neuron.

Before reaching axon terminal 14, a nerve signal conducted by axon 12 must first pass through a region referred to herein as a GABA gate complex 16, which includes a GABA$_A$ receptor complex (also called a GABA/benzodiazepine receptor). As described in more detail below, the GABA gate complex 16 normally maintains an inhibitory condition in the axon 12, so that a nerve impulse will pass through axon 12 and reach axon terminal 14 only if the electrochemical strength of the nerve impulse exceeds a threshold value.

During normal nerve signal activity, when CNS neuron 10 sends out an electrochemical impulse which exceeds the threshold value of the GABA gate complex 16, the electrochemical impulse results in the release of acetylcholine from axon terminal 14. Acetylcholine enters the extracellular fluid in the synaptic gap between terminal 14 and acetylcholine receptor 22, and reacts with the acetylcholine receptor 22. This triggers the opening of an ion channel that allows ions to enter the cingulate neuron 20, altering the electrochemical state in the interior of cingulate neuron 20.

The arrow with the legend "ACh→" next to axon 12 in FIG. 1 is not meant to imply that acetylcholine molecules travel through axon 12 to carry the nerve impulse. Instead, a nerve impulse is comparable to an electrical current passing through a wire. The "ACh→" arrow indicates that axon 12 is a cholinergic axon, which means that axon terminal 14 releases acetylcholine.

Cingulate neuron 20 has a glutamate axon trunk 24. After it leaves the main body of the cingulate neuron 20, axon trunk 24 splits into a main axon branch 26 and a minor axon branch 28. Both branches end in terminals that release glutamate when excited by a nerve impulse from the cingulate neuron 20.

The main axon branch 26 is likely to divide into more axon branches elsewhere, and each axon branch can interact with a neuron located elsewhere in the brain.

By contrast, the minor axon branch 28 travels to a GABAergic neuron 30. The GABAergic neuron 30 is presumed to be located reasonably close to the cingulate neuron 20, since one of the primary functions of the GABAergic neuron 30 is to regulate the excitation and activity of the cingulate neuron 20.

When cingulate neuron 20 fires off a nerve impulse through the major and minor axon branches, glutamate is emitted by axon terminal 29. The glutamate enters the extracellular fluid in the synapse. The glutamate reacts with and triggers an NMDA receptor 32 on the surface of GABAergic neuron 30. When the GABAergic neuron 30 is activated by that glutamate activity at its NMDA receptor 32, an electrochemical impulse travels through the GABAergic axon 34. That impulse results in the release of GABA from terminal 36 of axon 34. The GABA released by the axon terminal 36 reacts with the GABA gate 16 that is part of the cholinergic axon 12. When that happens, chloride ions enter cholinergic axon 12 via the open GABA ion channel. This alters the electrochemical state of the axon and inhibits further nerve impulses from travelling through axon 12. This helps to cleanly truncate the nerve impulse from the CNS neuron 10 and inhibits the additional release of acetylcholine at axon terminal 14.

The loop that includes the minor axon branch 28, the GABAergic neuron 30, and the GABA gate 16 in cholinergic axon 12 functions as a control circuit. When a CNS neuron 10 excites a cingulate neuron 20, part of the impulse emitted by the cingulate neuron 20 passes through the GABA neuron, which releases GABA in a manner which inhibits acetylcholine axon 12. This suppresses any further release of acetylcholine at synaptic receptor 22.

Based on various pieces of evidence, including experimental data gathered by the Inventor, it appears that in this kind of neural control circuit, the cingulate neuron 20 maintains a constant or repetitive pattern of discharge activity so that it provides a relatively steady or frequent low-level stimulation through the minor axon branch 28 which interacts with GABAergic neuron 30. This signal is not strong enough to trigger glutamate release at other, more distant locations in the brain, at the various terminals (not shown) of the major axon branch 26. Instead, the low-level repetitive discharge by cingulate neuron 20 apparently serves the sole purpose of maintaining a low level of GABA release by GABAergic neuron 30, which in turn maintains an inhibitory state at GABA gate 16. That inhibitory state prevents low-level currents from passing through axon 12 and triggering the release of acetylcholine at axon terminal 14. The inhibitory state maintained by the GABA gate 16 can only be overcome by a surge of current from CNS neuron 10 greater than the threshold value required to pass through the GABA gate 16 and reach terminal 14.

Such a surge will trigger the emission of a full-scale nerve signal by cingulate neuron 20. That nerve impulse, which will pass through axon trunk 24, will be strong enough to send a full-strength signal through the main axon branch 26 to interact with other nerve cells. It will also send a signal through the minor axon branch 28. It is suspected that a full-strength signal passing through minor axon branch 28 may be strong enough to trigger a high level of GABA release, which is powerful enough not just to maintain the normal low-level inhibitory state in GABA gate 16, but to arrest a full-strength bioelectric current passing through axon 12 toward terminal 14.

The postulated interconnections and the postulated low-level excitation of GABAergic neuron 30 by constant or repetitive low-level glutamate release at axon terminal 29 offer an explanation of how an NMDA antagonist can cause injury to neurons in the cingulate/retrosplenial cortex. They also offer an explanation of how such injury can be prevented by either anticholinergic or GABAmimetic drugs. When an NMDA antagonist such as PCP, MK-801, ketamine, or tiletamine blocks activity at NMDA receptor complex 22 on GABA neuron 30, it disrupts and turns off the release of GABA by GABAergic neuron 30. This in turn abolishes the normal and healthy inhibitory activity at the GABA gate 16, which the cingulate neuron 20 depends upon for protection against overstimulation by acetylcholine signals from CNS neuron 10. Based on evidence gathered by the Inventor using anti-cholinergic drugs, it appears that cholinergic overstimulation is the direct cause of the pathological changes in cingulate neuron 20; anti-cholinergic agents that block cholinergic receptor 22 prevent cholinergic overstimulation, as described and claimed in the parent application, Ser. No. 424,548 (issued as U.S. Pat. No. 5,034,400).

The foregoing discussion, which is based on experimental evidence gathered by the Inventor, also offers an explanation of how certain types of GABAmimetic agents (including diazepam and barbiturates) can help protect cingulate and retrosplenial neurons. However, as discussed above, barbiturates and diazepam act by different mechanisms, and they are not equally effective in restoring an inhibitory state at GABA gate 16. Barbiturates, by themselves, can open the chloride channel associated with GABA receptor 16, even if no GABA is present. By contrast, diazepam cannot open the chloride channel by itself; it can only strengthen the ability of GABA to open the chloride channel. Diazepam depends upon molecules of GABA being present in the synaptic fluid which bathes the GABA binding site at a GABA receptor complex.

When an NMDA antagonist is administered to an animal, the blocking action of the NMDA antagonist at NMDA receptor 32 abolishes the stimulus that causes GABAergic neuron 30 to release GABA. Therefore, when an NMDA antagonist is used, there will be little or no GABA present in the synaptic fluid which bathes the GABA receptor site at GABA gate 16. Under this circumstance, when little or no GABA is present in the synaptic fluid at GABA gate 16, the ability of diazepam to restore GABAergic inhibition at the gate is compromised. By contrast, the direct agonist action of barbiturates enables them to fully restore GABAergic inhibition at GABA gate 16 and fully protect against cholinergic overstimulation of cingulate neuron 20.

Both of these assertions—diazepam is unable to provide adequate protection against vacuole formation in cingulate neurons, while barbiturates provide complete protection—have been proven by experimental evidence. That experimental evidence is the basis of this invention. The effectiveness of barbiturates in providing full protection against the toxic side effects of NMDA antagonists has been demonstrated, and the experimental results are scientifically clear and legally sufficient to support this invention. As mentioned above, the validity of this invention does not rest upon the simplified depiction provided in FIG. 1, or in the postulated interconnections or events discussed in the portion of the specification which accompanies FIG. 1.

The experimental data is displayed in Table 1. The procedures used to gather those data are described in detail in Examples 1 and 2. In all animals, MK-801 (a strong NMDA antagonist) was injected subcutaneously at a constant dosage (0.4 mg of drug per kg of animal body weight) that had previously been shown to cause cerebrocortical pathomorphological changes in 100% of the treated animals. Control rats received only MK-801. Experimental animals received MK-801, then 10 minutes later were given a subcutaneous injection of diazepam (Valium) or a barbiturate (pentobarbital, secobarbital, or thiamylal) in various doses. The rats were sacrificed 4 hours after drug treatment, and brain sections from the cingulate cortex were examined histologically to determine the number of cingulate or retrosplenial neurons that contained vacuoles, which can be easily detected using a light microscope. The results, compiled in Table 1, are expressed as percentages, based upon the average number of neurons containing vacuoles in a group treated with both MK-801 and a barbiturate or diazepam, divided by the number of neurons containing vacuoles in animals treated with MK-801 only. In control animals treated with MK-801 without a safening agent, it was common for about 60 to 70 neurons in each brain section to contain vacuoles; in animals treated with safening agents, the number of neurons with vacuoles decreased.

As can be seen, diazepam (Valium) reduced vacuole formation by about 50% when administered at 1 mg/kg. However, at doses up to seven times higher than the 1 mg/kg effective dose, no

TABLE I

Protection against vacuole forming effects of MK-801 (0.4 mg/kg sc)

| Anti-vac Drug | Dose (Mg/kg sc) | Vacuoles (%)* |
|---|---|---|
| Pentobarbital | 5 | 100 |
|  | 10 | 80 |
|  | 15 | 46 |
|  | 20 | 0 |
|  | 30 | 0 |
|  | 50 | 0 |
| Secobarbital | 5 | 100 |
|  | 10 | 100 |
|  | 15 | 80 |
|  | 20 | 35 |
|  | 25 | 0 |
|  | 30 | 0 |
|  | 50 | 0 |
| Thiamylal | 10 | 100 |
|  | 20 | 100 |
|  | 30 | 78 |
|  | 40 | 42 |
|  | 50 | 0 |
|  | 60 | 0 |
| Diazepam | 1 | 51 |
|  | 5 | 42 |
|  | 7 | 46 |

*Mean number of vacuolated neurons in experimental brains as % of those in controls. n = 6 experimental rats per dose, compared to 48 control rats.

substantial increase in protection was conferred.

In additional experiments involving even higher doses, diazepam still could not confer complete and effective protection against vacuole formation even when administered at 20 mg/kg. At that dosage, the number of cingulate neurons having vacuoles tended to be smaller, but the vacuoles in affected neurons grew larger. Since it is difficult to quantify that effect, those data are not included in the Table.

By contrast, all three barbiturates offered complete protection against vacuole formation when administered at moderate dosages (about 2 and 3 times the lowest dosage that showed any positive effect). Pentobarbital began to show some benefit at a dosage of 10 mg/kg; by the time the dosage was increased to 20 mg/kg, which is still a moderate and reasonable dosage in the context of preventing brain damage due to conditions such as stroke or cardiac arrest, it offered 100% protection against vacuole formation. Secobarbital began to show some benefit at 15 mg/kg; at 25 mg/kg, it offered 100% protection. Thiamylal began to show some benefit at 30 mg/kg; by the time the dosage was increased to 50 mg/kg, it provided 100% protection.

These experimental results indicate that barbiturates which are capable of functioning as GABA agonists in the absence of GABA are much more effective in preventing neurotoxic damage caused by NMDA antagonists, when compared to benzodiazepine drugs that can only potentiate the effects of GABA when GABA is present.

Accordingly, this invention discloses a method for reducing or preventing the neurotoxic side effects of NMDA antagonists. This method comprises the administration of (1) a dosage of an NMDA antagonist which can protect the brain against excitotoxic damage, in conjunction with (2) a barbiturate which acts as a direct GABA agonist, in a quantity which prevents the formation of vacuoles in cingulate or retrosplenial cortical neurons, which would be caused by the NMDA antagonist without the safening agent.

This invention also discloses a composition of matter, comprising a mixture of an NMDA antagonist and a barbiturate, wherein the NMDA antagonist is present in a dosage that can protect the central nervous system against excitotoxic damage, and wherein the barbiturate acts as a direct GABA agonist and is present in a dosage that prevents the formation of vacuoles or the induction of heat shock proteins in cingulate or retrosplenial cortical neurons which would be created by the NMDA antagonist in the absence of the barbiturate.

As used herein, the terms "NMDA antagonists" and "barbiturates" include pharmaceutically acceptable salts and analogs of those agents which have the intended effects described herein. The term "pharmaceutically-acceptable salts" embraces salts commonly used to form alkali metal salts or addition salts of free acids or free bases. The nature of the acid or base used to form the salt is not critical, provided that it is non-toxic and does not substantially interfere with the pharmaceutical activity of the active agent as described herein. Examples of acids which may be employed to form pharmaceutically acceptable acid addition salts include inorganic acids such as hydrochloric acid, sulphuric acid and phosphoric acid, and organic acids such as maleic acid, succinic acid and citric acid. Other salts include salts with alkali metals or alkaline earth metals, such as sodium, potassium, calcium and magnesium. All of these salts may be prepared by conventional means.

Administration of the agents of this invention can be by any technique capable of introducing the compounds into the bloodstream of a human or veterinary patient, including oral administration or intravenous, intramuscular and subcutaneous injections. The active compound is usually administered in a pharmaceutical formulation such as in a liquid carrier for injection.

It is necessary to administer the NMDA antagonist and the barbiturate in a conjunctive manner so that the barbiturate safener can exert its safening activity at GABA receptors while the NMDA antagonist is exerting its own neuroprotective activity at NMDA receptors. However, this does not require that both agents must be mixed together or administered simultaneously or immediately sequential to each other. A moderate delay (such as several minutes) can occur between the administration of the two different agents. In addition, they can be administered by separate means. For example, a patient suffering a stroke might receive a bolus injection of an NMDA antagonist as quickly as possible, and shortly thereafter might be injected with a barbiturate safener by means of an intravenous drip.

It should be recognized that, since barbiturates can suppress respiratory functions, the use of barbiturates in conjunction with NMDA antagonists to prevent excitotoxic brain damage should be done only when a patient is supported on a respiratory support machine.

EXAMPLES

Example 1

Testing Barbiturates and Diazepam at Varying Dosages

Adult female Sprague Dawley rats, approximately 4 months old, were used in these experiments. It was previously established that MK-801 produced the vacuole effect in 75% of the animals at 0.2 mg/kg, and in 100% at doses of 0.3 and 0.4 mg/kg, when the MK-801 was injected subcutaneously (sc). In the present experiment, MK-801 was administered at a dose of 0.4 mg/kg sc, a dosage more than high enough to produce vacuoles in all animals that were not treated with a safener.

Control animals (n=48) were treated with MK-801 only. Experimental animals received MK-801, then 10 minutes later were given a subcutaneous injection of diazepam (Valium) or a barbiturate (pentobarbital, secobarbital, or thiamylal) in various doses (n=6 for each dosage group).

It was previously established (Olney et al 1989) that the vacuole effect becomes clearly observable within 4 hours following MK-801 treatment. Therefore, the rats were anesthetized and sacrificed by perfusion fixation of the CNS at 4 hours following MK-801 treatment. Their brains were processed by methods described in Olney 1971, permitting histopathological evaluation by light microscopy to determine the number of cingulate or retrosplenial neurons that contained vacuoles. The tissue samples were evaluated using numerical codes, by an experienced histopathologist who had no knowledge of the treatment conditions for any given tissue sample.

The results, compiled in Table 1, are expressed as percentages, based upon the average number of neurons containing vacuoles in a group treated with both MK-801 and a barbiturate or diazepam, divided by the number of neurons containing vacuoles in animals treated with MK-801 only. In all control animals treated with MK-801 without a safening agent, vacuoles were present in at least some neurons. It was common for about 60 to 70 neurons in each brain section to contain vacuoles. In animals treated with safening agents, the number of neurons with vacuoles decreased.

Diazepam (Valium) reduced vacuole formation by roughly 50% when administered at 1 mg/kg. However, at doses up to seven times higher than the 1 mg/kg effective dose, no increase in protection was conferred.

In additional experiments involving higher dosages, diazepam still could not confer complete and effective protection against vacuole formation even when administered at 20 mg/kg. At that dosage, the number of cingulate neurons having vacuoles tended to be smaller, but the vacuoles in affected neurons grew larger. Since it is difficult to quantify that effect, those data are not included in the Table.

In contrast to diazepam, all three barbiturates offered complete protection against vacuole formation when administered at moderate dosages (about 2 and 3 times the lowest dosage that showed any positive effect). Pentobarbital began to show some benefit at a dosage of 10 mg/kg; by the time the dosage was increased to 20 mg/kg, it offered 100% protection against vacuole formation. Secobarbital began to show some benefit at 15 mg/kg; at 25 mg/kg, it offered 100% protection. Thiamylal began to show some benefit at 30 mg/kg; by the time the dosage was increased to 50 mg/kg, it provided 100% protection.

Example 2

Analysis of Heat Shock Proteins

Adult rats were treated with MK-801 (0.4 mg/kg sc) as described in Example 1. Control rats (n=6) received only MK-801, and experimental rats (n=6) received the same dos of MK-801 followed 10 minutes later by pentobarbital at 20 mg/kg, a dosage sufficient to prevent vacuole formation in 100% of the rats treated. Control and experimental rats were sacrificed 24 hours later and their brains were studied using an immunostaining procedure using antibodies that bind to a 72 kilodalton heat shock protein described in Sharp et al 1990. In all control rats, a prominent expression of heat shock protein was detected; in all rats treated with both MK-801 and pentobarbital, no detectable quantities of the heat shock protein were found.

Thus, there has been disclosed a class of barbiturates which function as safening agents to allow the safe and effective use of NMDA antagonists as therapeutic agents.

The barbiturate safening agents of this invention provide complete and reliable protection, superior to the partial protection provided by diazepam. This invention therefore satisfies all of the objectives set forth herein. Although this invention has been described with respect to certain specific embodiments, the details of these embodiments are not to be construed as limitations. Various equivalents and modifications may be made without departing from the spirit and scope of this invention, which is limited only by the claims.

REFERENCES

Aebischer, B., et al, "Synthesis and NMDA Antagonist Properties of the Enantiomers of CPP and of the Unsaturated Analog CPP=ene," *Helvetica Chemica Acta* 72: 1043–1051 (1989)

Adelman, G. (ed.), *Encyclopedia of Neurosciences* (Birkhauser, Boston, 1987)

Akaike, N., et al, "Kinetic properties of the pentobarbitone gated chloride current in frog sensory neurons," *J. Physiol. (London)* 394: 85–98 (1987)

Allen, H. L., and Iversen, L. L., "Phencyclidine, dizocilpine, and cerebrocortical neurons," *Science* 247: 221 (1990)

Boast, C. A., "Neuroprotection after brain ischemia: role of competitive NMDA antagonists," *Neurology and Neurobiology* 46: 691–698 (1988)

Carter, C., et al, *J. Pharmacology and Experimental Therapeutics* 247: 1222–1232 (1988)

Carter, C., et al, *European J. Pharm.* 164: 611–612 (1989)

Clifford, D. B. et al, "Ketmaine and MK-801 prevent deegeneration of thalamic neurons induced by focal cortical seizures," *Exp Neurology* 105: 272–279 (1989)

Currie, R. W. and White, F. P., *Science* 214: 72 (1981)

Goodman, L. S. and Gilman, A., *The Pharmacological Basis of Therapeutics* (5th ed., Macmillan, New York, 1975)

Herrling, P. L., et al, "NMDA antagonistic properties of the enantiomers of CPP and CPP-ene," *Soc. Neurosci. Abstr.* 15: 327 (1989)

Honore, T., et al, "Quinoxalinediones: potent competitive non-NMDA glutamate receptor antagonists," *Science* 241: 701–703 (1988)

Honore, T., et al, "Quisqualate receptor specific quinoxalinedione (FG 9202, NBQX) blocks kainate induced responses," abstract, *J. Neurochem.* 52 (Suppl.): S42-A (1989)

Kemp, J. D., et al, "Non-competitive antagonists of excitatory amino acid receptors," *Trends in Neurosci.* 10: 294 (1987)

Labruyere, J., et al, "NMDA antagonists induce pathomorphological changes in cerebrocortical neurons," *Neurosci. Abst.* 15: 761 (1989)

MacDonald, R. L. and Barker, J. L., "Different actions of anti-convulsant and anesthetic barbiturates revealed by use of cultured mammalian neurons," *Science* 200: 775–777 (1978)

Magbagbeola, J. A. O. and Thomas, N. A., "Effect of Thiopentone on Emergence Reactions to Ketamine Anesthesia," *Canadian Anaesthes. Soc. J.* 21(3): 321–324 (1974)

Olney, J. W., "Glutamate-induced neuronal necrosis in the infant mouse hypothalamus: an electron microscopic study," *J. Neuropathol. Exp. Neurol.* 30: 75–90 (1971)

Olney, J. W., "Excitatory amino acids and neuropsychiatric disorders," *Biol. Psychiatry* 26: 505–525 (1989)

Olney, J. W., et al, "Pathological changes induced in cerebrocortical neurons by phencyclidine and related drugs." *Science* 244: 1360–1362 (1989)

*Physicians Desk Reference*, 40th Edition (Medical Economics Co., 1986)

Rothman, S. M., and Olney, J. W., "Glutamate and the Pathophysiology of Hypoxia-Ischemic Brain Damage," *Annals of Neurology* 19(2): 105–111 (1986)

Sharp, F. R., et al, *Soc. for Neuroscience Abstracts* 16:1122 (1990)

Sheardown, M. J., et al, "NBQX a specific non-NMDA receptor antagonist, shows neuroprotective effects against cerebral ischemia," abstract, published in *Proceedings of the First International Conference on Therapy with Amino Acids and Analogs*, Vienna, Aug. 7–12, 1989

Zorumski, C. F. and Isenberg, K. E., "Insights into the Structure and Function of GABA-Benzodiazepine Receptors: Ion Challens and Psychiatry," *Am. J. Psychiatry* 148(2): 162–173 (1991)

I claim:

1. A composition of matter, comprising a mixture of an NMDA antagonist and a barbiturate, wherein the NMDA antagonist is present in a dosage that can protect central nervous system neurons against excitotoxic neuronal death, and wherein the barbiturate acts as a direct GABA agonist and is present in an effective dosage that can prevent vacuole formation and induction of heat shock proteins in cingulate or retrosplenial cortical neurons which would be caused by administration of the NMDA antagonist without the barbiturate.

2. A method for preventing NMDA antagonists from generating vacuoles or inducing heat shock protein expression in cingulate or retrosplenial cortical neurons, comprising the step of administering to a susceptible mammal, in conjunction with an NMDA antagonist capable of causing vacuole formation or inducing heat shock protein expression in cingulate or retrosplenial cortical neurons, a therapeutically effective amount of a barbiturate which acts as a direct agonist of gamma-aminobutyric acid at gamma-aminobutyric acid/benzodiazepine receptors in the central nervous system.

3. In the method of using an NMDA antagonist to reduce hypoxic or ischemic damage to a mammalian central nervous system, the improvement consisting of co-administering, along with an NMDA antagonist which reduces hypoxic or ischemic damage but which also causes neurotoxic side effects, a therapeutically effective quantity of a second pharmaceutical agent comprising a barbiturate which acts at gamma-amino-butyric acid receptors and which prevents neurotoxic side effects of NMDA antagonists.

4. The method of claim 3 wherein the NMDA antagonist comprises a non-competitive NMDA antagonist which binds to a binding site in an NMDA receptor complex other than an N-methyl-D-aspartate binding site.

5. The method of claim 4 wherein the non-competitive NMDA antagonist functions as an agonist at phencyclidine receptors.

6. The method of claim 5 wherein the non-competitive NMDA antagonist comprises 5-methyl-10,11-dihydro-5H-dibenzo[a,d]cyclohepten- 5,10-imine, commonly called MK-801, or a salt or analog thereof.

7. The method of claim 5 wherein the pharmaceutical agent is selected from the group consisting of phencyclidine, ketamine, tiletamine, and dextromethorphan, and salts and analogs thereof.

8. The method of claim 4 wherein the non-competitive NMDA antagonist comprises a pharmaceutical agent that reacts with the polyamine binding site or the glycine binding site of the NMDA receptor complex.

9. The method of claim 8 wherein the pharmaceutical agent is selected from the group consisting of 4-benzylalpha-(p-hydroxy-phenyl)-beta-methyl-1-piperidine-ethanol, halogenated kynurenic acid, and (±)-2-(4-chlorophenyl)- 4-[(4-fluorophenyl)methyl]-1-piperidine ethanol, and salts and analogs thereof.

10. The method of claim 3 wherein the NMDA antagonist comprises a pharmaceutical agent which functions as a competitive antagonist at N-methyl-D-aspartate binding sites in NMDA receptor complexes.

11. The method of claim 10 wherein the pharmaceutical agent is selected from the group consisting of 2-amino-4-methyl-5-phosphono- 3-pentenoic acid, 4-phosphonomethyl)-2-piperidinecarboxylic acid, 3-(2)-carboxypiperazine-4-yl)-propyl-1 -phosphonate, and salts and analogs thereof.

12. The method of claim 3 wherein the NMDA antagonist comprises a pharmaceutical agent which functions as a broad-spectrum competitive antagonist at NMDA receptors and at non-NMDA excitatory amino acid receptors.

13. The method of claim 12 wherein the pharmaceutical agent is selected from the group consisting of quinoxalinediones and halogenated kynurenic acid, and salts and analogs thereof.

14. The method of claim 3 wherein the barbiturate is selected from the group consisting of pentobarbital and secobarbital and salts and analogs thereof.

15. The method of claim 3 wherein the barbiturate comprises a thiobarbiturate.

16. The method of claim 15 wherein the thiobarbiturate comprises thiamylal or a salt or analog thereof.

* * * * *